United States Patent [19]

Dufresne et al.

[11] Patent Number: 5,204,500
[45] Date of Patent: Apr. 20, 1993

[54] ERGONOMETRIC STETHOSCOPE CHESTPIECE

[75] Inventors: Joel R. Dufresne, St. Paul; Alan P. Dieken, St. Paul; Curt Hostager, deceased, late of St. Paul, all of Minn., by Ray S. Hostager legal representative

[73] Assignee: Minnesota Mining and Manufacturing Company, St. Paul, Minn.

[21] Appl. No.: 658,099

[22] Filed: Feb. 20, 1991

[51] Int. Cl.⁵ .................. A61B 7/02; H04R 25/00
[52] U.S. Cl. .................. 181/131; 181/137; 381/67
[58] Field of Search .......... 181/131, 137; 381/67; D24/134

[56] References Cited

U.S. PATENT DOCUMENTS

| | | | |
|---|---|---|---|
| D. 323,394 | 1/1992 | Casto et al. | D24/134 |
| 2,212,368 | 7/1950 | Allen | 429/82 |
| 2,893,507 | 7/1959 | Friedman | 181/137 |
| 3,765,503 | 10/1973 | Speidel | 181/137 |
| 3,790,712 | 2/1974 | Andries | 381/67 |
| 4,071,694 | 1/1978 | Pfeiffer | 381/67 |
| 4,170,717 | 10/1979 | Walshe | 381/67 |
| 4,254,302 | 3/1981 | Walshe | 381/67 |
| 4,440,258 | 4/1984 | Packard | 181/137 |
| 4,723,555 | 2/1988 | Shue | 128/715 |
| 4,878,501 | 11/1989 | Shue | 128/715 |

*Primary Examiner*—Michael L. Gellner
*Assistant Examiner*—Eddie C. Lee
*Attorney, Agent, or Firm*—Gary L. Briswold; Walter N. Kirn; William D. Bauer

[57] ABSTRACT

An ergonometric chestpiece for a stethoscope adapted to receive auscultatory sounds from a body and adapted to be coupled to an earpiece for a user. The chestpiece is adapted to be grasped by a thumb and at least one finger of the user. The chestpiece has a bottom surface which is generally planar and is adapted to be placed near the body for receiving the auscultatory sounds. The chestpiece has an upper portion opposite the bottom surface. The upper portion has a raised center portion defining left and right gripping surfaces which form recesses defined by the left and right gripping surfaces and by a surface generally parallel to but opposite the bottom surface. The left and right gripping surfaces are adapted to receive the thumb and the at least one finger of the user. Left and right gripping surfaces along with the surface generally parallel to but opposite the bottom surface forms a physical stop for the thumb and the at least one finger from contacting the body when the thumb and the at least one finger grasp the raised center of the upper portion. The gripping surfaces may be defined by left and right walls disposed generally normal to the bottom surface. The left and right walls may be concave. The ergonometric chestpiece may be generally circular and the left and right walls are cylindrically concave around axes generally orthogonal to the bottom surface. The top surface of the raised center portion may be sloped with respect to the bottom surface, the top surface being closer to the bottom surface at the front of the chestpiece than at the rear of the chestpiece.

13 Claims, 4 Drawing Sheets

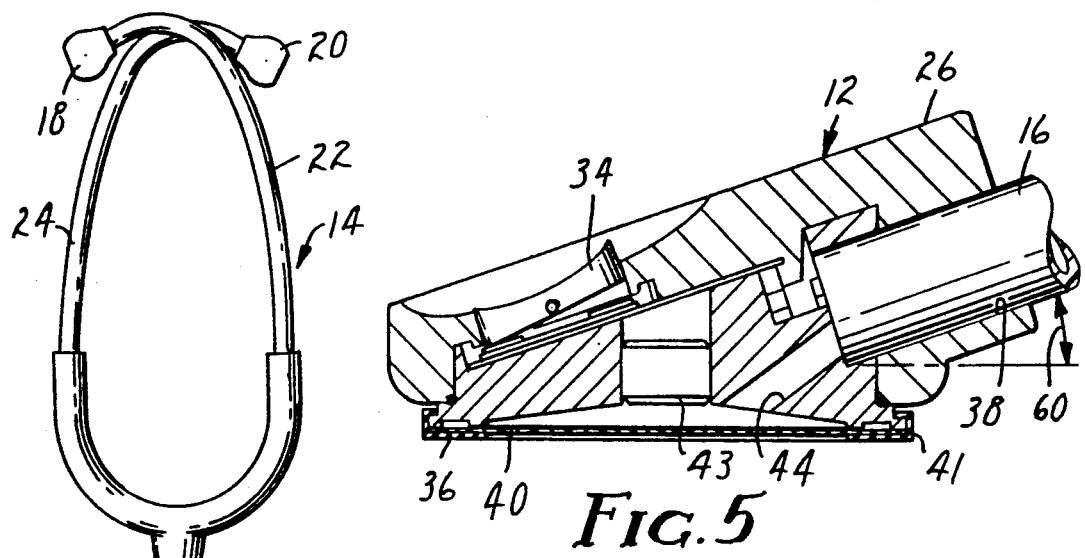
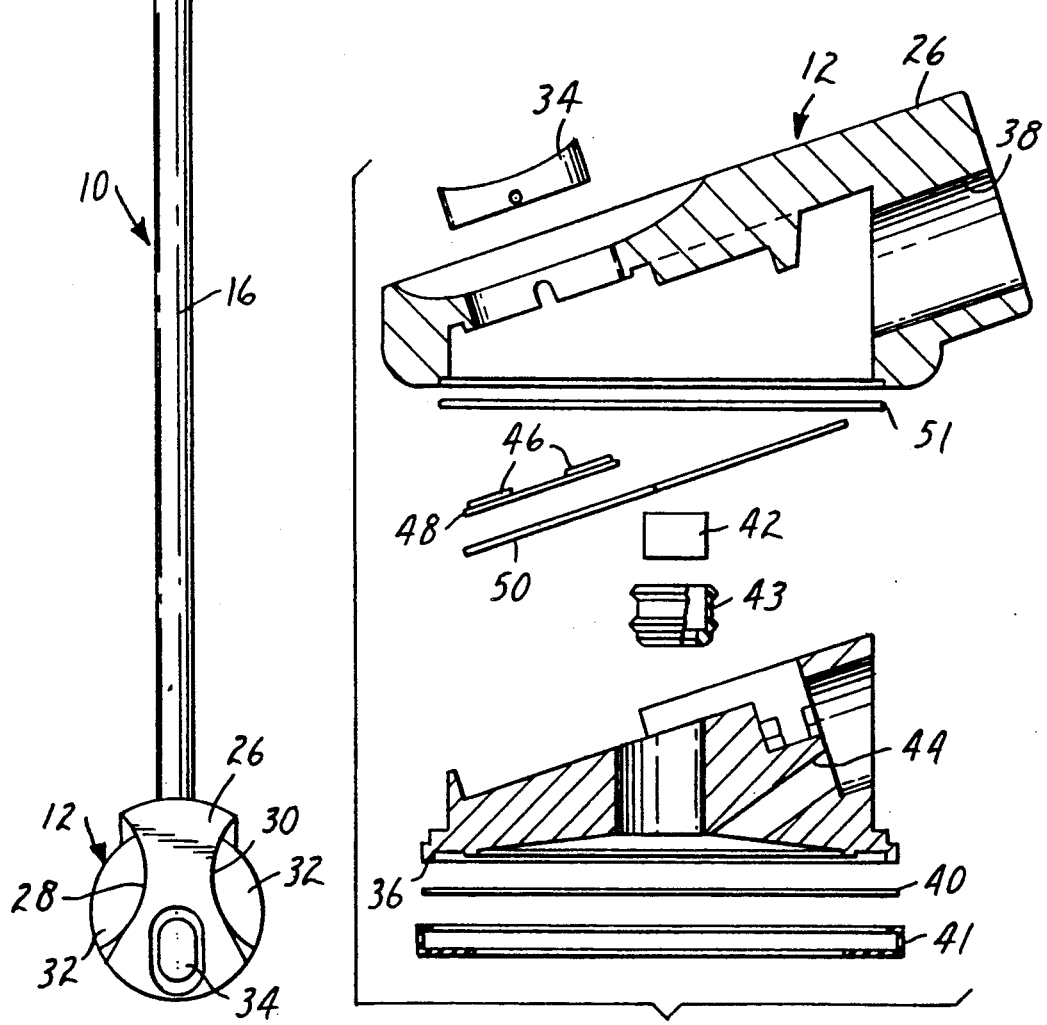

ERGONOMETRIC STETHOSCOPE CHESTPIECE

BACKGROUND OF THE INVENTION

The present invention relates generally to stethoscopes and, more particularly, to chestpieces for stethoscopes, especially electronic stethoscopes having operational controls located on the chestpiece.

Stethoscopes have long been used by physicians to monitor auscultatory sounds. Typically stethoscopes have been comprised of a head or chestpiece, a sound transmission mechanism and an earpiece assembly. The chestpiece is adapted to be placed against the skin of a patient for gathering the auscultatory sounds. The sound transmission mechanism transmits the gathered sound to the earpiece where the physician may monitor the sound.

The chestpiece of conventional auditory stethoscopes are usually quite simple physically. They are usually round disk shapes sometimes dual sided, top and bottom, to allow either side of the chestpiece to contact the skin of the patient, perhaps for the gathering of auscultatory sounds in different frequency ranges.

U.S. Pat. No. 4,071,694, Pfeiffer, Stethoscope, (assigned to the assignee of the present invention) describes a stethoscope which has both an electronic and an acoustic capability. The chestpiece of the stethoscope described in the Pfeiffer patent has a conventional shape and achieves a conventional function. The chestpiece is round and generally flat making the stethoscope appear and handle similarly, and has ergonometrics similar to, conventional stethoscopes.

Recently, the auditory sound gathering, transmission and delivery functions of stethoscopes have been supplemented or supplanted by electronic gathering or transmission.

The incorporation of electronic circuitry into the stethoscope has been a considerable design problem for the engineer. Typically, the electronic circuitry increases the physical size of the stethoscope package. Either the size of the chestpiece is increased in size dramatically or an additional enclosure to house the electronics is located between the chestpiece and earpiece assembly or both. In both of these cases, the resulting stethoscope is bulky, cumbersome to use and not easily storable between uses. The result, thus, is a stethoscope which is distinctly not ergonometric.

The problem of making a stethoscope, especially an electronic stethoscope ergonometric can be seen by reference to U.S. Pat. No. 3,790,712, Andries, Electronic Stethoscope System. The Andries patent describes an electronic stethoscope which has a chestpiece sized and shaped like a large rectangular, cumbersome box. This large, cumbersome box houses the electronic circuitry of the stethoscope. The box has a projecting member 15 with a forward lip portion 16 for engagement with a skin surface. This projecting member 15 has a conically shaped interior wall with a centrally located sound opening 18.

The stethoscope described in U.S. Pat. No. 4,170,717, Walshe, Electronic Stethoscope, has a chestpiece having an elongated housing 20 carrying a body piece 21 which includes an annular ring 21a to be placed against a patient's body. A thin diaphragm 22 extends across the opening formed by ring 21a and is acoustically coupled to a microphone 23. Again, the chestpiece of the stethoscope described in Walshe '717 is large, bulky and has a generally elongated rectangular shape rounded on one end.

The chestpiece 120 of the stethoscope described in U.S. Pat. No. 4,254,302, Walshe, Electronic Stethoscope, has an annular upper portion 160, a relatively larger annular lower portion 161 and a reduced diameter immediate control portion 162 adapted to be interdigitally grasped, particularly with the doctor's first and second fingers. The controls of the electronic stethoscope are positioned on the reduced diameter immediate control portion 162 for protection.

The stethoscope described in U.S. Pat. No. 4,723,555, Shue, Multi-Functional Radio/Wire Stethoscope Apparatus, and U.S. Pat. No. 4,878,501, Shue, Multi-Functional Radio/Wire Stethoscope Apparatus, has a chestpiece with a diaphragm on one side and a bell on the other designed for gathering auscultatory sounds. The chestpiece generally is shaped to have a truncated cone on each side with the open end of the cone adapted for contacting the patient's skin. The truncated section of the cones are coupled together with a cylinder forming a circular portion with a smaller diameter than the open end of the cones.

U.S. Pat. No. 4,440,258, Packard, Tunable Stethoscope, (assigned to the assignee of the present invention) describes a stethoscope with a chestpiece (stethoscope head) having a body member having a first generally bell-shaped recess, a diaphragm, a suspension member for connecting the diaphragm to the body member, and an immobilizing means located within the first recess. The suspension member affords movement of the diaphragm in a direction generally perpendicular to the plane of the diaphragm without the shape of or lateral tension in the diaphragm changing substantially. The movement of the diaphragm allows the stethoscope to be tunable with respect to auscultatory sounds.

The chestpiece of the stethoscope described in the Packard patent has a body member 11 formed of conventional material. The body member 11 has a substantially disk like portion 18 and a column 19 emanating therefrom. The top 20 of column 19 is substantially flat. Front section 21 of column 19 is sloped away from top 20, is concave in configuration and is curved to meet the top surface of disk like portion 18. Side sections 22 and 23 and back section 24 are arcuate in configuration. The shape of body member 11 permits the physician to grasp column 19 from the top with the index finger being placed on front section 21 and each of the thumb and the middle finger adjacent disk 18 on opposite sides of column 19 with a fitting 15 passing between those fingers.

The column 19 of the chestpiece of the stethoscope described in the Packard patent allows the chestpiece to be easily grasped by the physician. The column 19 is generally cylindrical with concave side walls. The cylindrical shape of column 19 limits the precise positioning and indexing of the fingers and space for positioning controls and indicators.

SUMMARY OF THE INVENTION

The chestpiece of the present invention is easily grasped by the physician and fits comfortably into the physician's hands. The top surface of the base member prevents the physician's fingers from directly contacting the patient's skin while affording ample holding and grasping capacity. The raised center portion has a physical stop which prevents the fingers of the physician from sliding with respect to the chestpiece and, perhaps sliding off of the chestpiece. In a preferred embodiment of the invention, the physical stop in the chestpiece is provided by substantially vertical concave side walls formed by gripping surfaces which flare out and prevent the forward or backward slide of the fingers of the physician.

The raised center portion of the chestpiece slopes downward toward the front of the chestpiece allowing the chestpiece to comfortably be nested into the palm of the hand of the physician.

With the sloped top of the raised center portion of the stethoscope chestpiece fits into the palm of the physician's hand and the physician's fingers comfortably holding the side walls and being prevented from slipping forward, having a finger available to operate one or more operational controls. These controls may be located, preferably in a recessed fashion, on top of the forward portion of the raised center portion.

Thus, in one embodiment the present invention provides an ergonometric chestpiece for a stethoscope adapted to receive auscultatory sounds from a body and adapted to be coupled to an earpiece assembly, or binaural assembly, for a user. The chestpiece is adapted to be grasped by a thumb and at least one finger of the user. The chestpiece has a bottom surface which is generally planar and is adapted to be placed near or in comfortable contact with the body for receiving the auscultatory sounds. The chestpiece has an upper portion opposite the bottom surface. The upper portion has a raised center portion defining left and right gripping surfaces which form recesses defined by the left and right gripping surfaces and by a surface generally parallel to but opposite the bottom surface. The left and right gripping surfaces are adapted to receive the thumb and the at least one finger of the user, respectively. The raised center portion form a physical stop for the thumb and the at least one finger from contacting the body when the thumb and the at least one finger grasp the raised center of the upper portion.

In a preferred embodiment, the gripping surfaces are defined by left and right walls disposed generally normal to the bottom surface. In a preferred embodiment, the left and right walls are concave. In a preferred embodiment, the ergonometric chestpiece is generally circular and the left and right walls are cylindrically concave around axes generally orthogonal to the bottom surface. In a preferred embodiment, the top surface of the raised center portion is sloped with respect to the bottom surface, the top surface being closer to the bottom surface at the front of the chestpiece than at the rear of the chestpiece.

In a preferred embodiment, the ergonometric chestpiece further has at least one operational control placed on the raised center portion in a position easily manipulated by a finger of the user. In a preferred embodiment, at least one operational control is mounted on the top surface of the raised center portion of the chestpiece. In a preferred embodiment, at least one control is placed on the forward portion of the raised center portion of the chestpiece. In a preferred embodiment, the chestpiece has a plurality of controls all located on the forward portion of the top surface of the raised center portion, the plurality of controls all being positioned for manipulation by a finger of the user. In a preferred embodiment, each of the plurality of controls is recessed to prevent inadvertent actuation of a control function.

BRIEF DESCRIPTION OF THE DRAWINGS

The foregoing advantages, construction and operation of the present invention will become more readily apparent from the following description and accompanying drawings in which:

FIG. 1 is a top plan view illustrating a stethoscope incorporating the chestpiece according to one embodiment of the present invention;

FIG. 5 is a side cross sectional view of an embodiment of the chestpiece of the present invention;

FIG. 6 is a side explosion view of an embodiment of the chestpiece of the present invention;

DETAILED DESCRIPTION OF THE PREFERRED EMBODIMENTS

Figure 2:
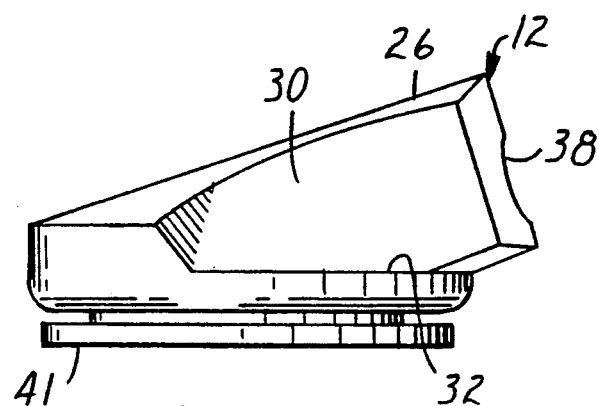
FIG. 2 is a side view of an embodiment of the chestpiece of the present invention.

The stethoscope 10 illustrated in FIG. 1 consists of a chestpiece 12, or stethoscope head, a binaural assembly 14 and a connecting tube 16. The binaural assembly 14 has two earpieces 18 and 20 adapted to fit in or near the ear of a user, typically a physician or other medical professional. Tubes 22 and 24, generally acoustic tubes, couple earpieces 18 and 20, respectively to connecting tube 16 which in turn is coupled to chestpiece 12.

The sound transmission system of stethoscope 10 may be entirely acoustic as is well known in the art. However, it is also contemplated that the sound transmission system of stethoscope 10 could also be electronic. In this situation, an acoustic to electronic transducer, a microphone 42, would be located along the acoustic sound transmission path, typically in or very near the chestpiece 12, and even more typically in the chestpiece 12 positioned near the bottom surface 36, shown in FIG. 5, of the chestpiece 12 so as to be near the source of auscultatory sounds. Electronic means would then typically amplify, or otherwise process, the electrical signal. The electrical signal may be transmitted electrically to an electrical to acoustic transducer, a speaker, typically located nearer the earpieces 22 and 24 of the stethoscope 10 or to an external signal processing device. Of course, a stethoscope of a combination acoustic and electronic, or dual acoustic and electronic, is also contemplated.

In the preferred embodiment, stethoscope 10 is of dual acoustic and electronic construction. An acoustic path exists from chestpiece 12, along connecting tube 16 through tubes 22 and 24 to earpieces 18 and 20 of binaural assembly 14. In addition, a microphone is positioned within chestpiece 12. The electrical signal obtained from the microphone is amplified and processed by conventional electronic circuitry located within chestpiece 12. Electrical wires transmit the processed electrical signal within and along connecting tube 16. A speaker is located at juncture of tube 22 and 24 and connecting tube 16. This speaker transforms the auscultatory sounds back to the acoustic domain where tubes 22 and 24 transmit the acoustic sounds to earpieces 18 and 20.

Figure 3:
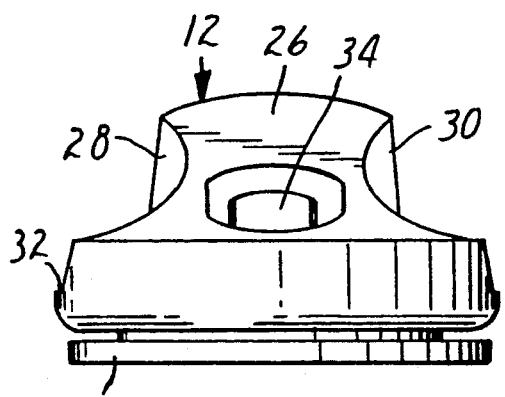
FIG. 3 is a front view of an embodiment of the chestpiece of the present invention.

The top surface of chestpiece 12 is visible in FIGS. 1, 2 and 3 The bottom surface 36 of the chestpiece 12 is adapted to be placed near the source of auscultatory sound, or, in a preferred embodiment, comfortable contact the skin of the patient. Chestpiece 12 has a raised center portion 26 which is adapted to be grasped by the thumb and one of the fingers of the user, typically the thumb and middle finger. Left and right gripping surfaces 28 and 30 of the raised center portion 26 are adapted to engage the gripping appendages (thumb and finger) of the user. Gripping surfaces 28 and 30 are defined by walls which are concave generally along one or more axis generally orthogonal to the bottom surface of chestpiece 12 and further are defined by the surface 32 of the chestpiece 12 opposite the bottom surface. In a preferred embodiment, the walls defining gripping surfaces 28 and 30 are generally vertical. The area formed by the walls of gripping surfaces 28 and 30 and, preferably planar, surface 32 define left and right recesses which are adapted to receive the thumb and at least one finger of the user. These gripping surfaces 28 and 30 are preferably formed by concave cylindrical surfaces which flare outward toward the front, and preferably toward the rear, of the chestpiece 12.

The left and right recesses formed into raised center portion 26 allow gripping surfaces 28 and 30 to act as a physical stop which prevents the fingers or thumb of the user from sliding forward during use and eliminates the possibility of the the fingers and/or thumb slipping off of the chestpiece 12. This slippage could result in an interruption of the monitoring of auscultatory sounds and further could result in pain, embarrassment or lack of confidence to the user and/or the patient. The flaring of the concave shape of the gripping surfaces to an angle outward of directly forward in the chestpiece facilitates the physical stop. It is preferred that this angle be at least thirty degrees from straight forward and, still further preferably, this should be at least about forty-five degrees but, for comfort, substantially less than ninety degrees from straight forward on the chestpiece 12.

It is preferred that the ergonometric chestpiece 12 has a shape which is generally circular. Further, where the shape of chestpiece 12 is generally circular, the left and right walls formed by gripping surfaces 28 and 30 are preferred to be cylindrically concave around axes generally orthogonal to the bottom surface.

One or more operational controls, in this embodiment a rocker switch 34, is positioned on the top surface of the raised center portion 26. Rocker switch 34 is positioned roughly in the middle of raised center portion 26 generally forward of gripping surfaces 28 and 30. In this position, rocker switch 34 is easily available to be manipulated by the index finger of the user when gripping surfaces 28 and 30 are grasped by the user's thumb and middle finger. Typical uses of rocker switch 34 are to turn power to the stethoscope 10 on, or off, when the rocker switch 34 is rocked in a first direction, or a second direction, or similarly to increase, or decrease the volume of the auscultatory sound delivered to the user or control other functions as appropriate.

Figure 4:
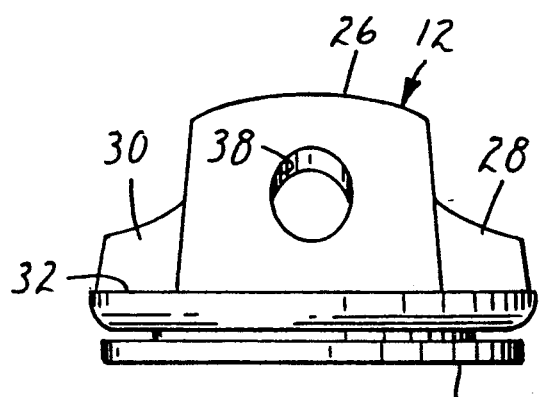
FIG. 4 is a rear view of an embodiment of the chestpiece of the present invention.
Figure 7:
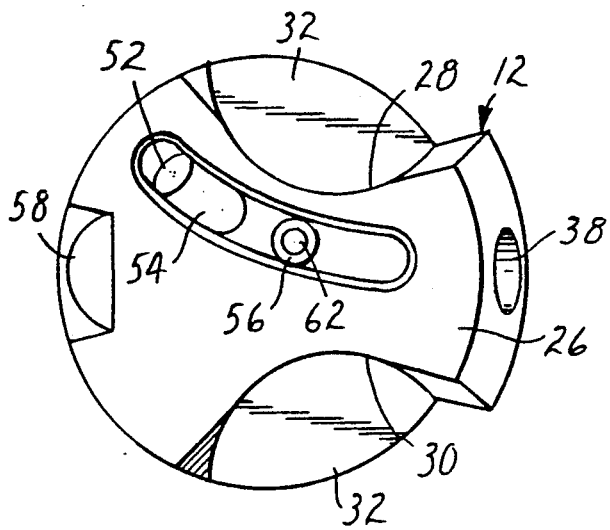
FIG. 7 is a top view of an alternative embodiment of the chestpiece of the present invention.
Figure 8:
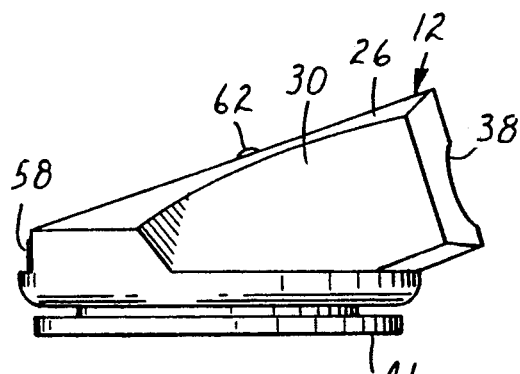
FIG. 8 is a side view of an alternative embodiment of the chestpiece of the present invention.
Figure 9:
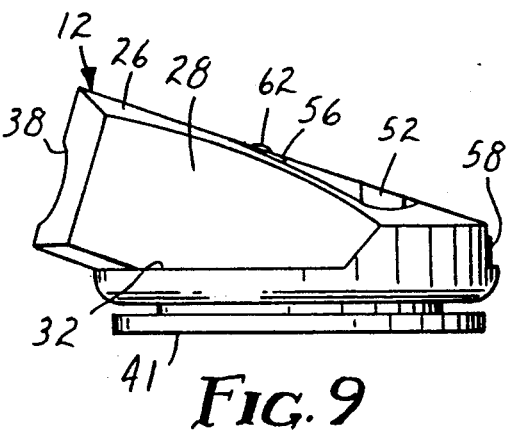
FIG. 9 is the opposite side view of an alternative embodiment of the chestpiece of the present invention.
Figure 10:
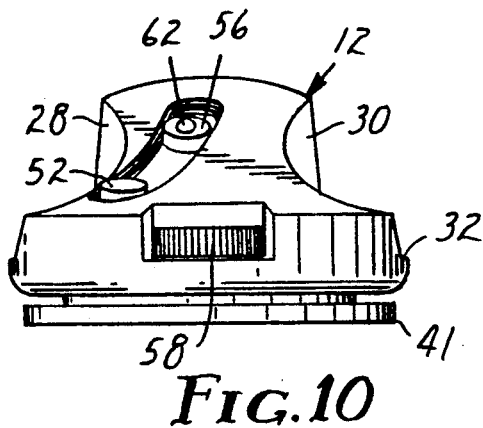
FIG. 10 is a front view of an alternative embodiment of the chestpiece of the present invention.

Detailed side, front and rear views of chestpiece 12 are illustrated in FIGS. 2, 3 and 4, respectively. Bottom surface 36, which is preferably generally planar, is adapted to be placed near the source of auscultatory sound, and preferably, adapted to be placed on the skin of the patient. Surface 32, helping to define the gripping recesses, is preferably also generally planar and parallel to the plane formed by bottom surface 36. As could be seen with respect to FIG. 1, chestpiece 12 has a raised center portion 26 into which gripping surfaces 28 and 30 are defined by walls. Again, the walls forming the gripping surfaces 28 and 30 flare to form a physical forward stop for the user's fingers.

The top surface of raised center portion 26 preferably is sloped downward from rear to front of chestpiece 12 to form a surface which may be easily held in the palm of the hand of the user and allow easy positioning under a garment or a medical drape. Thus, raised center portion 26 is higher, i.e., thicker, at the rear of the chestpiece 12 than at the front of the chestpiece 12.

Connecting tube 16 shown in FIG. 5 is coupled to chestpiece 12 at the rear of chestpiece 12 at opening 38 at an angle 60 positioning connecting tube 16 to minimize interference with the user and to not cause discomfort to the patient.

FIGS. 5 and 6 illustrate a side cross-sectional view and a side explosion view of a preferred embodiment of chestpiece 12. Bottom surface 36 is illustrated as being generally planar. A diaphragm 40 is held in place by diaphragm retainer 41 and is stretched across an opening in the bottom surface 36 which allows for the entry of auscultation sounds into the chestpiece 12. A microphone 42 is mounted by microphone holder 43 within chestpiece 12 and is positioned in close proximity to diaphragm 40. An acoustic passage 44 allows for the simultaneous transmission of acoustic signals. Rocker switch 34 is mounted on the forward part of raised center portion 26. Rocker switch 34 activates silicon rubber keypad with conductive rubber pads 46. When rocker switch 34 is pressed the conductive rubber pads 46 provide the switching or control function bridging conductive elements on printed circuit board 50. An O-ring 51 helps to seal the chestpiece 12 from ingress of contaminants.

FIGS. 7, 8, 9 and 10 illustrate an alternative embodiment of the chestpiece 12 of the present invention. As in the first embodiment, chestpiece 12 has a planar bottom surface 36, a raised center portion 26 which slopes downward toward the front and gripping surfaces 28 and 30. The embodiment of chestpiece 12 illustrated in these Figures differs with respect to the number, placement and form of the operational controls. It is preferred that the shape and separation of the operational controls be chosen for ease of identification by sight from the top of the chestpiece 12 and/or feel, in order to provide ease of operation and minimum erroneous or inadvertent operation.

A slide switch 52 is located in recess 54 on the top surface and in the forward portion of raised center portion 26. Push button switch 56 is also located within recess 54. Recess 54 itself is arcuate, skewing toward the outside edge of raised center portion 26 similar to the wall formed by gripping surface 28. Further, a rotary control 58, in a preferred embodiment a potentiometer, is positioned in a recess near the front edge of raised center portion 26 and chestpiece 12. The rotary action of control 58 is in a plane parallel to the plane of bottom surface 36. In a typical function, slide switch 52 may be used to control to function or mode of operation, such as the frequency response, of stethoscope 10, push button switch 56 may be used to control the power to the stethoscope 10 and rotary switch 58 may be used to control the volume of the stethoscope 10. The presence of power to stethoscope 10 is indicated by light emitting diode 62. All of these controls are easily accessible to and easily manipulated by the index finger of the user. Preferably, all of the controls and indicators can be read from the top of the chestpiece 12.

Figure 11:
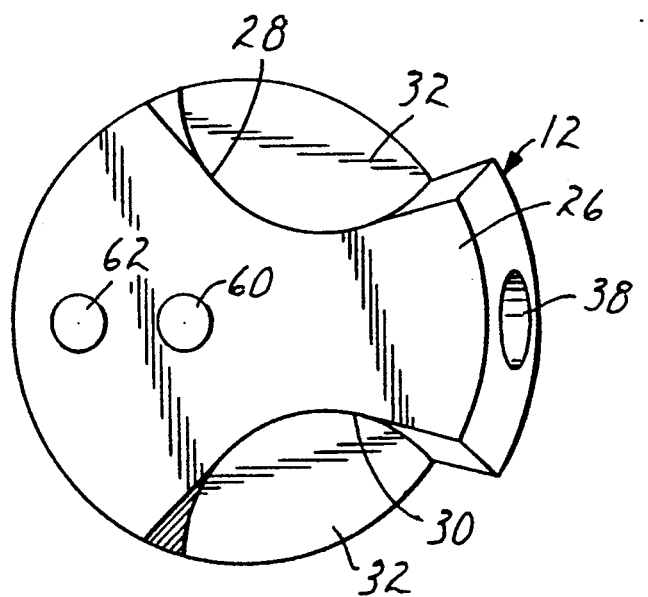
FIG. 11 is a top view of another alternative embodiment of the chestpiece of the present invention.
Figure 12:
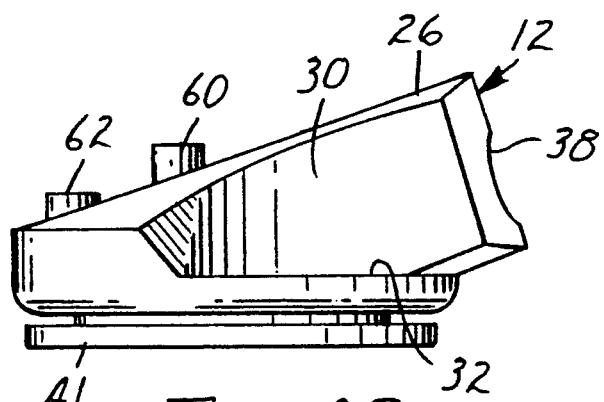
FIG. 12 is a side view of another alternative embodiment of the chestpiece of the present invention.
Figure 13:
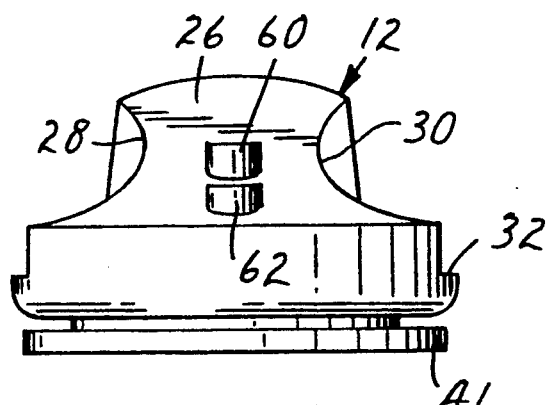
FIG. 13 is a front view of another alternative embodiment of the chestpiece of the present invention.

Another alternative embodiment of chestpiece 12 is illustrated in FIGS. 11, 12, and 13. As in the first two embodiments, chestpiece 12 has a planar bottom surface 36, a raised center portion 26 which slopes downward toward the front and gripping surfaces 28 and 30 defining recesses with the assistance of surface 32. The embodiment of chestpiece 12 illustrated in these Figures differs with respect to the number, placement and form of the operational controls and indicators.

In this embodiment, first and second push button switches 60 and 62 are located on the top surface and in the forward portion of raised center portion 26. Push button switch 60 may be used to control a first function or mode of operation, such as the frequency response, of stethoscope 10. Push button switch 62 may be used to control a second function or mode of operation, such as the power to the stethoscope 10. All of these controls are easily accessible to and easily manipulated by the index finger of the user.

Thus, chestpiece 12 functions quite ergonometrically in use by the physician or other health care professional.

The chestpiece 12 is easily grasped by the physician and fits comfortably into the physician's hands. The surface 32 on the base of the chestpiece 12 opposite from bottom surface 36 (as shown in FIG. 2) prevents the physician's fingers from directly contacting the patient's skin while affording ample holding and grasping capacity for manipulation of the chestpiece 12. The raised center portion 26 has a physical stop which prevents the fingers of the physician from sliding with respect to the chestpiece 12 and, perhaps sliding off of the chestpiece 12. The physical stop in the chestpiece 12 is provided by substantially vertical concave side walls which flare out toward the front, and preferably toward the rear, and prevent the forward or rearward slide of the fingers of the physician.

The raised center portion 26 of the chestpiece 12 slopes downward toward the front of the chestpiece 12 allowing the chestpiece 12 to be held comfortably in the palm of the hand of the physician and be easily positioned under a garment or medical drape.

With the sloped top of the raised center portion 26 of the stethoscope chestpiece 12 being held in the palm of the physician's hand and the physician's fingers comfortably holding the gripping surfaces 28 and 30 and being prevented from slipping forward, a finger is available to operate one or more operational controls. These controls may be located, preferably in a recessed fashion, on top of the forward portion of the raised center portion 26.

Thus, it can be seen that there has been shown and described a novel ergonometric stethoscope chestpiece. It is to be recognized and understood, however, that various changes, modifications and substitutions in the form and the details of the present invention may be made by those skilled in the art without departing from the scope of the invention as defined by the following claims.

What is claimed is:

1. An ergonometric chestpiece for a stethoscope adapted to receive auscultatory sounds from a body and adapted to be coupled to an earpiece assembly for a user, said chestpiece adapted to grasped by a thumb and at least one finger of said user, comprising:
    said chestpiece having a bottom surface which is generally planar adapted to be placed near said body for receiving said auscultatory sounds;
    said chestpiece having an upper portion opposite said bottom surface;
    said upper portion having a raised center portion defining left and right gripping surfaces forming recesses defined by said left and right gripping surfaces and by a surface generally parallel to but opposite said bottom surface, said recesses of said left and right gripping surfaces adapted to receive said thumb and said at least one finger of said user, respectively;
    said raised center portion forming a physical stop for said thumb and said at least one finger from contacting said body when said thumb and said at least one finger grasp said raised center of said upper portion;
    said gripping surfaces being defined by left and right walls, each having a concave surface arcuate about an axis generally normal to said bottom surface.

2. An ergonometric chestpiece as in claim 1 wherein said concave surfaces of said left and right walls face in opposite directions.

3. An ergonometric chestpiece as in claim 2 which is generally circular and wherein said left and right walls are cylindrically concave around axes generally orthogonal to said bottom surface.

4. An ergonometric chestpiece as in claim 2 wherein said chestpiece has a top surface opposite from said bottom surface and wherein the top surface of said raised center portion is sloped with respect to said bottom surface, said top surface being closer to said bottom surface at one edge of said chestpiece than at an opposite edge of said chestpiece.

5. An ergonometric chestpiece as in claim 4 which further comprises at least one operational control placed on said raised center portion in a position easily manipulated by a finger of said user.

6. An ergonometric chestpiece as in claim 5 wherein at least one said operational control is mounted on the top surface of said raised center portion of said chestpiece.

7. An ergonometric chestpiece as in claim 6 wherein said at least one control is placed on said raised center portion of said chestpiece.

8. An ergonometric chestpiece as in claim 7 wherein said chestpiece is coupled to said earpiece assembly at the rear of said chestpiece.

9. An ergonometric chestpiece as in claim 8 wherein said chestpiece has a plurality of controls all located on the forward portion of the top surface of said raised center portion, said plurality of controls all being positioned for manipulation by a finger of said user.

10. An ergonometric chestpiece as in claim 9 wherein each of said plurality of controls is recessed.

11. An ergonometric chestpiece as in claim 10 which further comprises a rotary central, planar with respect to said bottom surface, located at said one edge of said raised center portion of said chestpiece, said rotary control being capable of controlling of said stethoscope.

12. An ergonometric chestpiece as in claim 11 wherein said stethoscope has a frequency response and wherein said plurality of controls is limited to a first control being capable of controlling power to said stethoscope, a second control being capable of controlling the frequency response of said stethoscope and a third control being said rotary control.

13. An ergonometric chestpiece as in claim 8 which further comprises at least one light indicators located on said raised center portion and positioned for viewing from above said chestpiece.

* * * * *